(12) United States Patent
Irwin et al.

(10) Patent No.: US 8,583,728 B2
(45) Date of Patent: Nov. 12, 2013

(54) EXTENSIBILITY FOR MANIPULATION OF MEDICAL DATA

(75) Inventors: John H. Irwin, Marcellus, NY (US); Marshall W. Magee, Skaneateles, NY (US); Mark E. Pingel, Camillus, NY (US); Gary L. Arnold, Camillus, NY (US); David D. Gamble, East Syracuse, NY (US); David E. Rynkiewicz, Auburn, NY (US); Michael D. Hoch, North Syracuse, NY (US); James M. Robinson, Camillus, NY (US); Matthew J. Bobowski, Williamson, NY (US)

(73) Assignee: Welch Allyn, Inc., Skaneateles Falls, NY (US)

(*) Notice: Subject to any disclaimer, the term of this patent is extended or adjusted under 35 U.S.C. 154(b) by 261 days.

(21) Appl. No.: 13/076,487

(22) Filed: Mar. 31, 2011

(65) Prior Publication Data

US 2011/0246565 A1    Oct. 6, 2011

Related U.S. Application Data

(60) Provisional application No. 61/319,707, filed on Mar. 31, 2010.

(51) Int. Cl.
   *G06F 15/16* (2006.01)
(52) U.S. Cl.
   USPC .......................... 709/203; 709/217; 709/223

(58) Field of Classification Search
   USPC ........................................ 709/203, 217, 223
   See application file for complete search history.

(56) References Cited

U.S. PATENT DOCUMENTS

| | | | |
|---|---|---|---|
| 7,533,961 B2 * | 5/2009 | Kikuchi et al. | 347/41 |
| 2002/0145634 A1 | 10/2002 | Gueramy | |
| 2004/0087836 A1 | 5/2004 | Green | |
| 2004/0107118 A1 * | 6/2004 | Harnsberger et al. | 705/2 |
| 2005/0133027 A1 | 6/2005 | Elaz | |
| 2009/0044185 A1 * | 2/2009 | Krivopaltsev | 717/173 |
| 2009/0150768 A1 * | 6/2009 | Bae et al. | 715/248 |
| 2009/0222283 A1 | 9/2009 | Lassetter | |
| 2011/0165688 A1 * | 7/2011 | Dupoteau et al. | 436/55 |

OTHER PUBLICATIONS

International Search Report & Written Opinion in PCT/US2011/030631 mailed Sep. 29, 2011, 9 pages.

* cited by examiner

*Primary Examiner* — Phuoc Nguyen
(74) *Attorney, Agent, or Firm* — Merchant & Gould P.C.

(57) ABSTRACT

A method for extending a functionality of a computing device programmed to obtain physiological measurements from a patient includes: registering, at the computing device, a plug-in module, the plug-in module providing additional functionality for the computing device; using the plug-in module to communicate with a medical device; commanding the medical device to obtain physiological information from a patient; receiving data associated with the physiological information from the medical device; and transferring the data to a central repository.

17 Claims, 7 Drawing Sheets

EXTENSIBILITY FOR MANIPULATION OF MEDICAL DATA

RELATED APPLICATION

This application claims the benefit of U.S. Patent Application Ser. No. 61/319,707 filed on Mar. 31, 2010, the entirety of which (including all exhibits thereto) is hereby incorporated by reference.

BACKGROUND

Health care practitioners, such as nurses and physicians, use various types of health-care equipment to assist with the task of providing health care to a patient. Some health-care equipment is designed to perform multiple functions, such as temperature measurement and blood pressure measurement. Such multi-function equipment may be limited in functionality based on the types of activities and medical devices with which the equipment has been programmed to interface.

SUMMARY

In one aspect, a software platform for healthcare diagnostic applications includes: a computing device including memory and a processor that, when executing instructions stored on the memory, creates: a client-side framework defining elements for use by platform client applications; a composite application framework supporting extensible modules, the composite application framework supporting construction of composite applications in which functionality is implemented by a container application which hosts plug-in modules to support specific diagnostic functions; a plug-in module extending platform applications; a composite application combining base application code with plug-in modules to support a set of clinical functions; and a domain-specific framework for defined clinical measurement domains, wherein the domain-specific framework shares certain common code and resources with other modules and contain domain-specific expandable sets of sensor measurement plug-ins which obtain physiologic data of a type covered by a domain.

In another aspect, a method for extending a functionality of a computing device programmed to obtain physiological measurements from a patient includes: registering, at the computing device, a plug-in module, the plug-in module providing additional functionality for the computing device; using the plug-in module to communicate with a medical device; commanding the medical device to obtain physiological information from a patient; receiving data associated with the physiological information from the medical device; transferring the data to a central repository.

In yet another aspect, a computer-readable storage medium encodes instructions that, when executed by a processor, cause the processor to perform steps including: registering, at a computing device, a plug-in module, the plug-in module providing additional functionality for the computing device; using the plug-in module to communicate with a medical device; commanding the medical device to obtain physiological information from a patient; receiving data associated with the physiological information from the medical device; transferring the data to a central repository.

DETAILED DESCRIPTION

The present disclosure relates to communicating and storing diagnostic tests with the purpose of supporting the extensibility of the test type and contained diagnostic measurements.

In creating a multi-purpose diagnostic application, one challenge is the ability to add and support new diagnostic test types and measurements over time. Examples of diagnostic test types which could be supported include: vital signs, resting ECG, spirometry, exercise ECG, holter, etc. A primary concern in adding new test types and measurements to an existing system is how to handle communicating and storing these new types while minimizing the changes to existing code and database structures.

The goal of this disclosure is to create an extensible communication and storage pattern for test and measurement types such that no changes are needed to these definitions as new diagnostic test and measurement types are added to the application.

A common solution to the problem of adding new diagnostic test types and measurement types to an existing application is to modify the storage subsystem's database structure to accommodate the new types, and to modify application code to recognize and handle the new types. This has the advantage of not requiring database or application code changes, allowing a new test type and/or measurement types to be added by the addition of the plug-in module.

Test result data is arranged in a common "Test" class (data structure) which contains a collection of one or more measurement-specific classes. The Test class contains attributes and operations which are common to all tests no matter what test type they are. These common attributes include things like: a unique test identifier, the test type, the date/time the test was taken, the user who performed the test, etc. The common attributes are understood and used by a wide range of code which stores, manages, and summarizes test results. The measurement-specific classes are derived from a common "Measurement" class such that they support a set of common operations to be performed on them by code which has no knowledge of the measurement-specific data. There is one or more test/measurement-specific plug-ins to support each new diagnostic test type/measurements. These plug-ins support the following functions:

The plug-ins register an XML-based information schema for the measurements they support within the storage subsystem. This schema is used by the storage subsystem to interpret the fields of the stored data in order to support storage, query, and retrieval operations.

The plug-ins define the measurement-specific classes, and implement conversion methods to convert to/from the measurement-specific class instances from/to the measurement-specific information schema used by the storage subsystem.

The plug-ins support test/measurement-specific operations, such as: capture, editing, and visualization of test/measurement-specific data.

Extensibility is gained through the following mechanisms: Test results are communicated using common test and measurement data structures which encapsulate test/measurement-specific data in a standardized encoding per a registered schema.

The storage subsystem supports the registration of test/measurement-specific information schema, allowing for the storage, query, and retrieval of the added types.

Operations, such as capture, editing, and visualization, which require knowledge of the encapsulated test/measurement-specific data, are contained within test/measurement-specific plug-in code.

For example, a new test can be created as follows. The new test is populated with necessary data including the patient (Patient), test type (TestType), test measurements (test.Measurements) taken, and any other available data. Example pseudo code for creation of the test is provided below:

```
test.StartDateTime = DateTimeOffset.Now;
test.TestType = VitalsConstants.TestType;
test.PatientRef.Entity = patient;
test.Measurements.Add(new HeartRateMeasurement( ) {
    TakenDateTime = DateTimeOffset.Now,
    HeartRate = 65,
    Unit = HeartRate.Unit.BeatsPerMinute
};
```

A function call is used to save it to persistent storage. This new test can be used as a plug-in to extend the functionality of existing medical devices.

This systems and methods disclosed herein allow the construction of a multi-purpose diagnostic application in which new diagnostic test types and measurement types can be added without wholesale changes to application code and storage mechanisms. New diagnostic test types and measurement types can be added through the addition of application plug-ins which define and support these new types.

Figure 1:
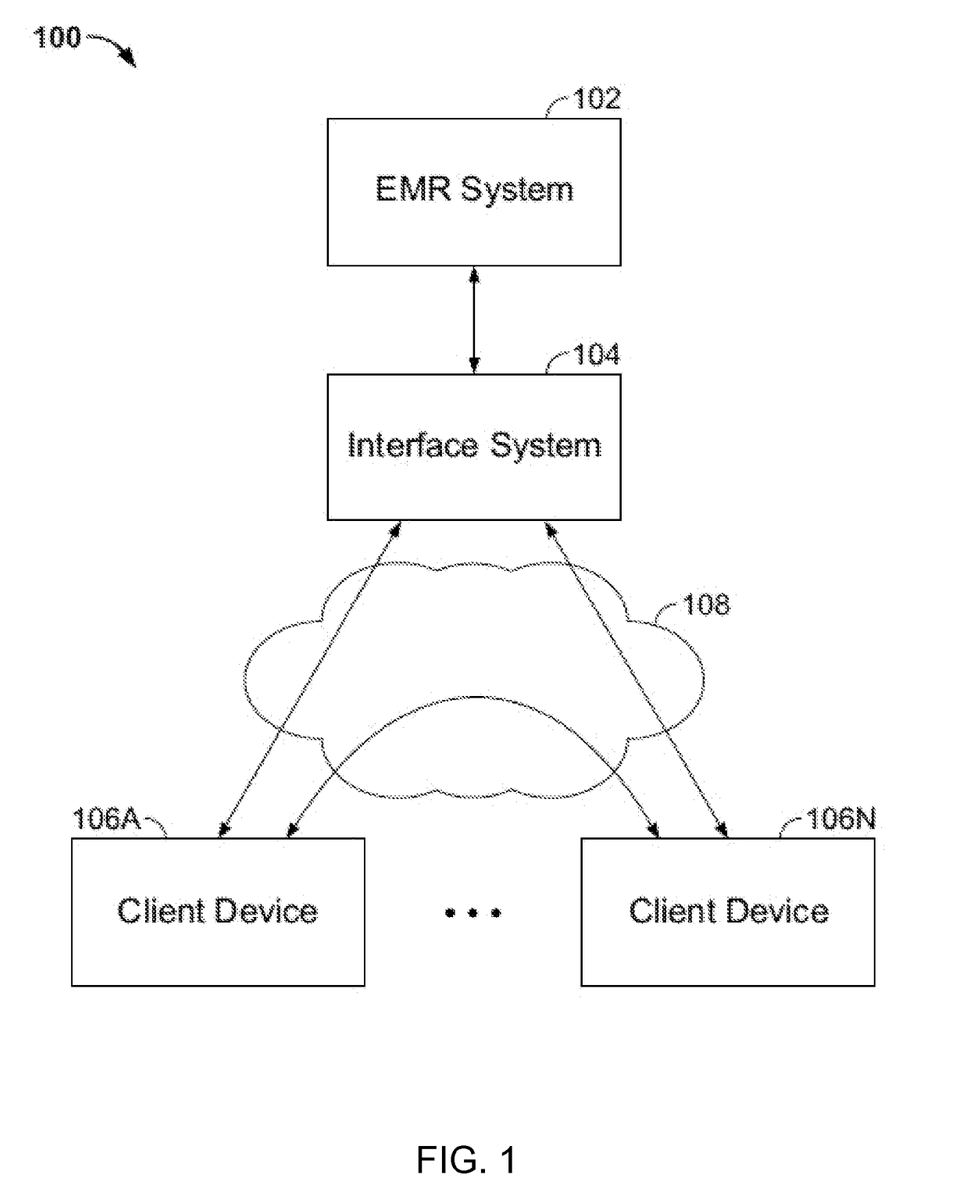
FIG. 1 shows an example system for collecting measurements of physiological parameters of patients.

FIG. 1 is a block diagram illustrating an example system 100 for collecting measurements of physiological parameters of patients. As illustrated in the example of FIG. 1, the system 100 comprises an Electronic Medical Records (EMR) system 102, an interface system 104, a set of client devices 106A-106N (collectively, "client devices 106"), and a network 108.

In one example, the system 100 is a CONNEX® system from Welch Allyn, Inc. of Skaneateles Falls, N.Y., although other systems can be used.

The network 108 is an electronic communication network that facilitates communication between the client devices 106 and the between the client devices 106 and the interface system 104. An electronic communication network is a set of computing devices and links between the computing devices. The computing devices in the network use the links to enable communication among the computing devices in the network. The network 108 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices. In various embodiments, the network 108 includes various types of links. For example, the network 108 can include wired and/or wireless links. Furthermore, in various embodiments, the network 108 is implemented at various scales. For example, the network 108 can be implemented as one or more local area networks (LANs), metropolitan area networks, subnets, wide area networks (such as the Internet), or can be implemented at another scale.

The EMR system 102 is a computing system that allows storage, retrieval, and manipulation of electronic medical records. As used herein, a computing system is a system of one or more computing devices. A computing device is a physical, tangible device that processes data. Example types of computing devices include personal computers, standalone server computers, blade server computers, mainframe computers, handheld computers, smart phones, special purpose computing devices, and other types of devices that process data.

Each client device in the set of client devices 106 is a computing device. The client devices 106 can provide various types of functionality. For example, the set of client devices 106 can include one or more physiological monitor devices (such as the physiological monitor device 200). In addition, the set of client devices 106 can include one or more desktop, laptop, or wall-mounted devices. Such devices can have similar functionality to the physiological monitor device 200 but are stationary instead of portable, such as workstation devices (such as the VM workstation 450). In addition, the set of client devices 106 can include one or more monitor devices. Such monitor devices can display representations of physiological parameters. A monitor device could, for example, be used by a clinician to monitor the physiological parameters of multiple patients at one time.

The client devices 106 can communicate with each other through the network 108. In various embodiments, the client devices 106 can communicate various types of data with each other through the network 108. For example, in embodiments where the set of client devices 106 includes a set of physiological monitor devices and a monitor device, each of the physiological monitor devices can send data representing measurements of physiological parameters of patients to the monitor device. In this way, the monitor device can display representations of physiological parameters to a clinician.

The interface system 104 is a computing system that acts as an interface between the EMR system 102 and the client devices 106. Different EMR systems have different software interfaces. For example, the EMR system used by two different hospitals can have two different software interfaces. The interface system 104 provides a single software interface to each of the client devices 106. The client devices 106 send requests to software interface provided by the interface system 104. When the interface system 104 receives a request from one of the client devices 106, the interface system 104 translates the request into a request that works with the software interface provided by the EMR system 102. The interface system 104 then provides the translated request to the software interface provided by the EMR system 102. When the interface system 104 receives a response from the EMR system 102, the interface system 104 translates the response from a format of the EMR system 102 to a system understood by the client devices 106. The interface system 104 then forwards the translated response to an appropriate one of the client devices 106.

The client devices 106 can send various types of data to the interface system 104 for storage in the EMR system 102 and can receive various types of data from the EMR system 102 through the interface system 104. For example, in some embodiments, the client devices 106 can send measurements of physiological parameters to the interface system 104 for storage in the EMR system 102. In another example, a monitor device can retrieve past measurements of physiological parameters of patients from the EMR system 102 through the interface system 104.

Figure 2:
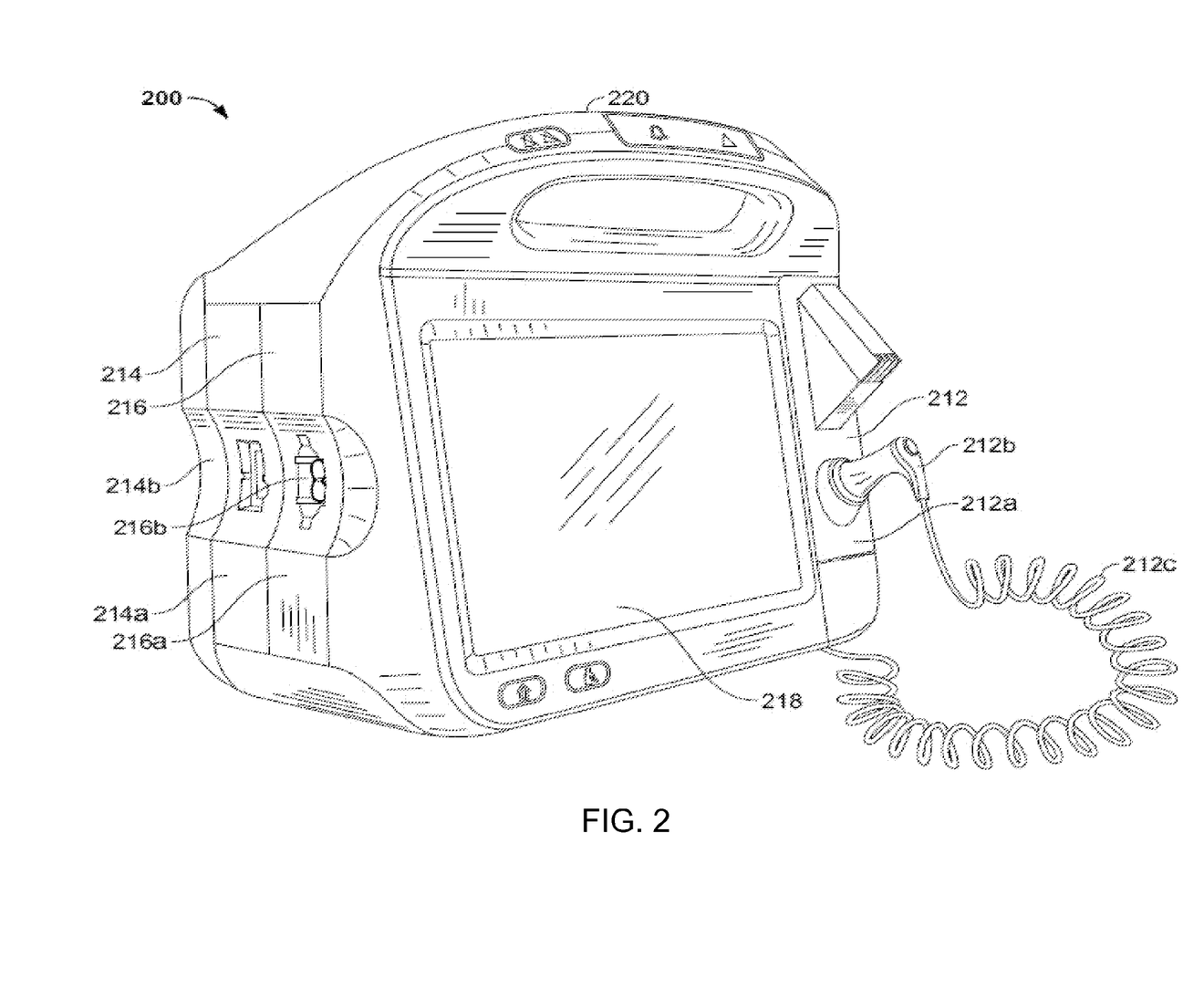
FIG. 2 shows an example physiological monitor device that can be used in the system illustrated in FIG. 1.

FIG. 2 illustrates a view of an example physiological monitor device 200. The physiological monitor device 200 is portable. The physiological monitor device 200 includes multiple health care equipment (HCE) modules. Each of the HCE modules is configured to measure one or more physiological parameters of a health-care recipient, also referred to herein as a patient.

A temperature measurement module 212 is accessible from the front side of the physiological monitor device 200. A SpO2 module 214 and a non-invasive blood pressure (NIBP) module 216 are accessible from a left hand side of the physiological monitor device 200. An upper handle portion 220 enables the physiological monitor device 200 to be carried by hand.

A front side of the physiological monitor device 200 includes a display screen 218 and an outer surface of the temperature measurement module 212. The temperature measurement module 212 is designed to measure the body temperature of a patient. As used in this document, a "module" is a combination of a physical module structure which typically resides within the physiological monitor device 200 and optional peripheral components (not shown) that typically attach to and reside outside of the physiological monitor device 200.

The temperature measurement module 212 includes a front panel 212a. The front panel 212a has an outer surface that is accessible from the front side of the physiological monitor device 200. The front panel 212a provides access to a wall (not shown) storing a removable probe (not shown), also referred to as a temperature probe, that is attached to a probe handle 212b. The probe and its attached probe handle 212b are tethered to the temperature measurement module 212 via an insulated conductor 212c. The probe is designed to make physical contact with a patient in order to sense a body temperature of the patient.

A left hand side of the physiological monitor device 200 includes an outer surface of the SpO2 module 214 and an outer surface of the NIBP module 216. The SpO2 module 214 is a HCE module designed to measure oxygen content within the blood of a patient. The NIBP module 216 is a HCE module designed to measure blood pressure of a patient.

As shown, the SpO2 module 214 includes a front panel 214a. The front panel 214a includes an outer surface that is accessible from the left side of the physiological monitor device 200. The front panel 214a includes a connector 214b that enables a connection between one or more peripheral SpO2 components (not shown) and a portion of the SpO2 module 214 residing inside the physiological monitor device 200. The peripheral SpO2 components reside external to the physiological monitor device 200. The peripheral SpO2 components are configured to interoperate with the SpO2 module 214 when connected to the SpO2 module 214 via the connector 214b. In some embodiments, the peripheral SpO2 components include a clip that attaches to an appendage of a patient, such as a finger. The clip is designed to detect and measure a pulse and an oxygen content of blood flowing within the patient.

As shown, the NIBP module 216 includes a front panel 216a having an outer surface that is accessible from the left side of the physiological monitor device 200. The front panel 216a includes a connector 216b that enables a connection between one or more peripheral NIBP components (not shown) and a portion of the NIBP module 216 residing inside the physiological monitor device 200. The peripheral NIBP components reside external to the physiological monitor device 200. The peripheral NIBP components are configured to interoperate with the NIBP module 216 when connected to the NIBP module 216 via the connector 216b. In some embodiments, the peripheral NIBP components include an inflatable cuff that attaches to an appendage of a patient, such as an upper arm of the patient. The inflatable cuff is designed to measure the systolic and diastolic blood pressure of the patient, the mean arterial pressure (MAP) of the patient, and the pulse rate of blood flowing within the patient.

The physiological monitor device 200 is able to operate within one or more workflows. A workflow is a series of one or more tasks that a user of the physiological monitor device 200 performs. When the physiological monitor device 200 operates within a workflow, the physiological monitor device 200 provides functionality suitable for assisting the user in performing the workflow. When the physiological monitor device 200 operates within different workflows, the physiological monitor device 200 provides different functionality.

When the physiological monitor device 200 is manufactured, the physiological monitor device 200 is configured to be able to operate within one or more workflows. After the physiological monitor device 200 is manufactured, the physiological monitor device 200 can be reconfigured to operate within one or more additional workflows. In this way, a user can adapt the physiological monitor device 200 for use in different workflows as needed.

In various embodiments, the physiological monitor device 200 operates within various workflows. For example, in some embodiments, the physiological monitor device 200 can operate within a monitoring workflow or a non-monitoring workflow. Example types of non-monitoring workflows include, but are not limited to, a spot check workflow and a triage workflow.

In example embodiments, the names for the workflows can be defined by the user. For example, the user can rename a "triage workflow" as "ED 3 North" or any other nomenclature as desired to provide more context to the user.

When the physiological monitor device 200 is operating within the monitoring workflow, the physiological monitor device 200 obtains a series of measurements of one or more physiological parameters of a single monitored patient over a period of time. In addition, the physiological monitor device 200 displays, on the display screen 218, a monitoring workflow home screen. The monitoring workflow home screen contains a representation of a physiological parameter of the monitored patient. The representation is based on at least one measurement in the series of measurements. A representation of a physiological parameter is a visible image conveying information about the physiological parameter.

For example, when the physiological monitor device 200 is operating within the monitoring workflow, the physiological monitor device 200 can obtain a blood pressure measurement of a single patient once every ten minutes for six hours. In this example, the physiological monitor device 200 displays a monitoring workflow home screen that contains a representation of the patient's blood pressure based on a most recent one of the temperature measurements. In this way, a user of the physiological monitor device 200 can monitor the status of the patient.

When the physiological monitor device 200 is operating within a non-monitoring workflow, the physiological monitor device 200 obtains a measurement of one or more physiological parameters from each patient in a series of patients. In addition, the physiological monitor device 200 displays a non-monitoring workflow home screen on the display screen 218. The non-monitoring workflow home screen contains a representation of the physiological parameter of a given patient in the series of patients. The representation is based on the measurement of the physiological parameter of the given patient.

In one example, when the physiological monitor device 200 is operating within a spot check workflow, the physiological monitor device 200 obtains blood pressure measurements from a series of previously-identified patients. In this other example, the physiological monitor device 200 displays a spot check workflow home screen containing a blood pressure measurement of a given patient in the series of previously-identified patients. In this way, a user of the physiological monitor device 200 can perform spot checks on the blood pressures of patients who have already been admitted to a hospital.

As used in this document, a patient is a previously identified patient when the physiological monitor device 200 stores information regarding the identity of the patient. In another example, when the physiological monitor device 200 is operating within a triage workflow, the physiological monitor device 200 can obtain a single blood pressure measurement from each patient in a series of unidentified patients as the patients arrive at a hospital. In this example, the physiological monitor device 200 displays a triage workflow home screen containing a representation of the patients' blood pressure based on the single blood pressure measurements of the patients. In this way, a user of the physiological monitor device 200 can perform triage on the series of unidentified patients as they arrive. As used in this document, a patient is an unidentified patient when the physiological monitor device 200 does not store information regarding the identity of the patient.

The monitoring workflow home screen is different than the non-monitoring workflow home screen. Further, as discussed below, the navigation options associated with the different workflows allows for efficient monitoring based on the environment in which the device is used. In various embodiments, the monitoring workflow home screen is different than the non-monitoring workflow home screen in various ways. For example, in some embodiments, the monitoring workflow home screen includes at least one user-selectable control that is not included in the non-monitoring workflow home screen. In other embodiments, a representation of a physiological parameter in the monitoring workflow home screen has a different size than a representation of the same physiological parameter in the non-monitoring workflow home screen.

Figure 3:
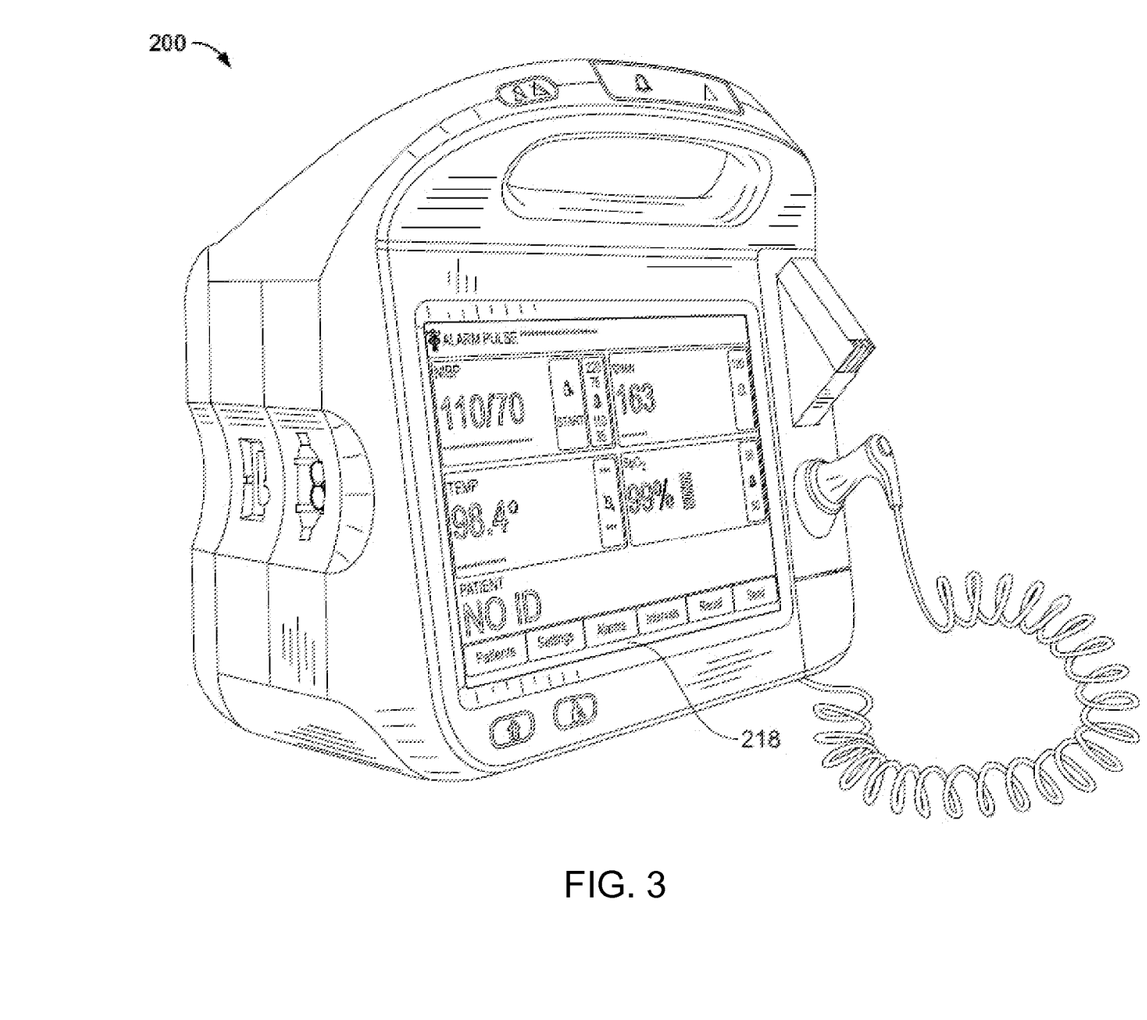
FIG. 3 shows an example user interface displayed on the display screen of the physiological monitor device of FIG. 2.

FIG. 3 illustrates an example user interface displayed on the display screen 218 of FIG. 2. The physiological monitor device 200 outputs and displays user interfaces discussed in this document on the display screen 218.

In some examples described herein, the physiological monitor device is a portable device. In other examples, the physiological monitor device is a non-portable device, such as a computing device like a workstation. Many configurations are possible.

Figure 4:
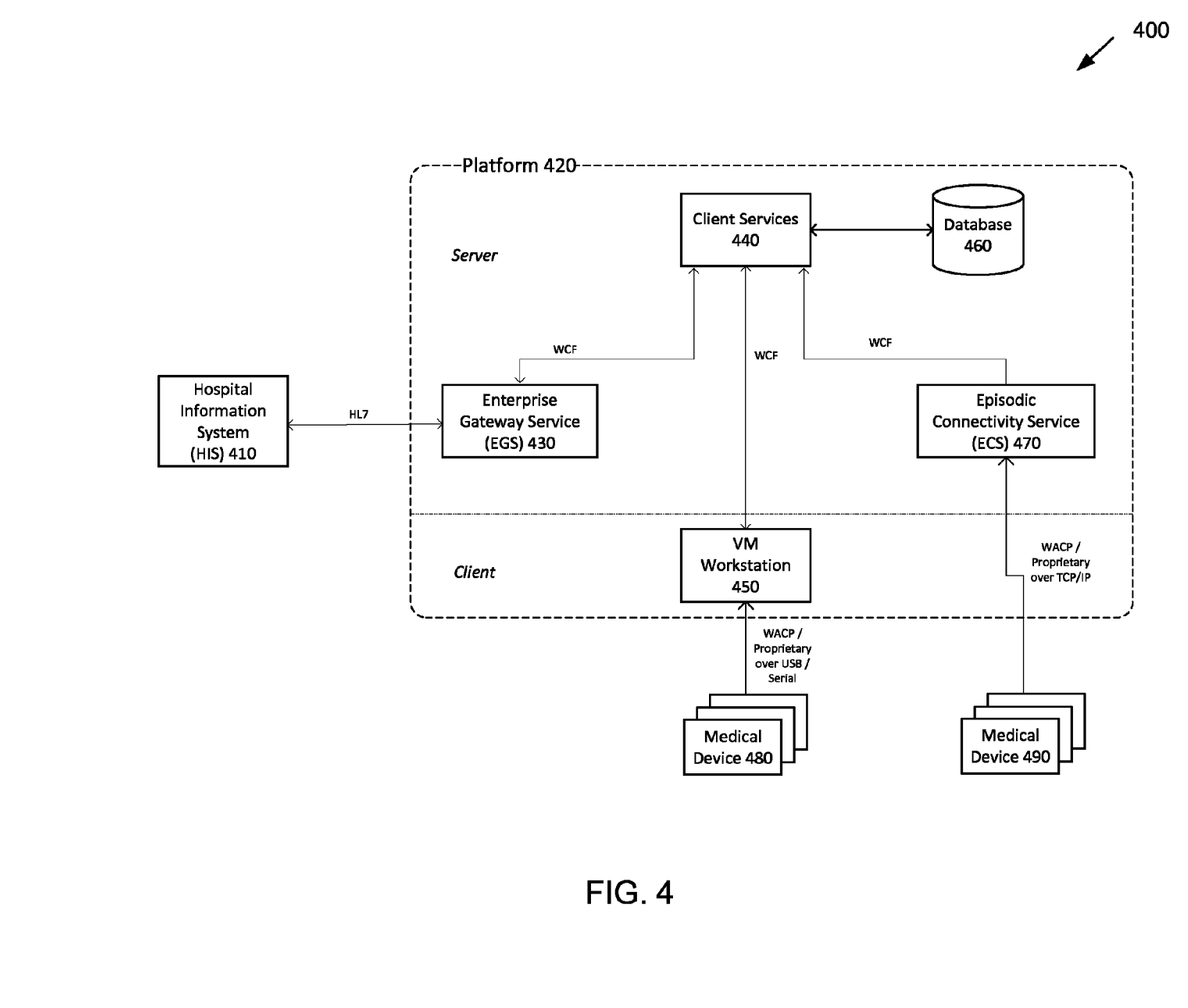
FIG. 4 shows another example system for collecting measures of physiological parameters of patients.

Referring now to FIG. 4, another example system 400 for collecting measurements of physiological parameters of patients is shown. The system 400 is similar to the system 100 described above, with the following distinctions.

The system 400 is a client/server, service-oriented architecture. A platform 420 in the system 400 provides various services, including the Enterprise Gateway Service (EGS) 430, Episodic Connectivity Service (ECS) 470, and the client services 440. Devices and client applications, such as a Vital Monitoring (VM) workstation 450 access these services via a wired or wireless network connection over known protocols and interfaces, such as the Windows Communication Foundation (or WCF), which is an application programming interface (API) in the .NET Framework for building connected, service-oriented applications. Other configurations are possible.

In a typical network topology, a single server machine hosts all of the client services 440. The server also hosts a Microsoft SQL Server database 460 which provides the persistent data store for the platform 420. All database access in the platform 420 is through the client services 440.

Medical devices 480, 490 (i.e., devices that interface or interact with a patient to obtain physiological data, such as the physiological monitor device 200) can connect to the platform 420 in two ways. Devices 490 can communicate indirectly with the client services 440 via the ECS 470 which provides the infrastructure for protocol and data transformation. Alternately, medical devices 480 can connect to the VM workstation 450 via a hardwired USB or standard serial connection.

In either scenario, the devices 480, 490 can communicate through known protocols, such as the Welch Allyn Communications Protocol (WACP). WACP uses a taxonomy as a mechanism to define information and messaging. Taxonomy can be defined as description, identification, and classification of a semantic model. Taxonomy as applied to a classification scheme may be extensible. Semantic class-based modeling utilizing taxonomy can minimize the complexity of data description management by limiting, categorizing, and logically grouping information management and operational functions into families that contain both static and dynamic elements.

The EGS 430 provides connectivity between the platform 420 and external systems for transfer of patient, visit and test information. The EGS 430 interacts with the client services 440 as well as external systems. The EGS 430 supports the industry standard HL7 protocol for communicating with the external systems, such as a Hospital Information System (HIS) 410.

In this example, the VM workstation 450 is an extensible client application built on the Windows Presentation Foundation (WPF) graphical subsystem for rendering user interfaces in Windows-based applications from Microsoft Corporation of Redmond, Wash. The VM workstation 450 provides a graphical user interface (UI) for patient and test management. The VM workstation 450 allows end users to acquire, visualize, update and save diagnostic medical data. As noted, devices (e.g., medical device 480) can connect to the VM workstation 450 via USB or serial connections. Plug-ins allow test data to be imported or acquired through direct control of the connected device. Plug-ins can also provide the ability to visualize and post-process the test data.

The example ECS 470 supports wired and wireless network-based device connectivity. The ECS 470 enables medical devices 490 to connect and communicate with the platform 420 via the network infrastructure. The ECS 470 communicates with the medical devices 490, receiving requests and processing them via interaction with the client services 440. In order to support new devices, the ECS 470 consumes plug-ins for communicating with and processing data.

The example EGS 430 supports interfacing with external hospital information systems (e.g., HIS 410) for the exchange of patient and test data. Default functionality allows data to be exported through HL7 messages or file I/O. The EGS 430 consumes plug-ins which transform test and measurement data into formats expected by the external systems. The EGS 430 can also be extended to support different network communication protocols that may be required by external systems.

In this example, the client services 440 provide basic data management services for test, patient and clinician data. These services are responsible for managing the majority of the data within the platform 420. The core services also support user authentication, server administration, error logging and a publish/subscribe service.

As described further below, one or more of the VM workstation 450, ECS 470 and EGS 430 can be extended by plug-ins using types and interfaces defined for the platform 420.

Figure 5:
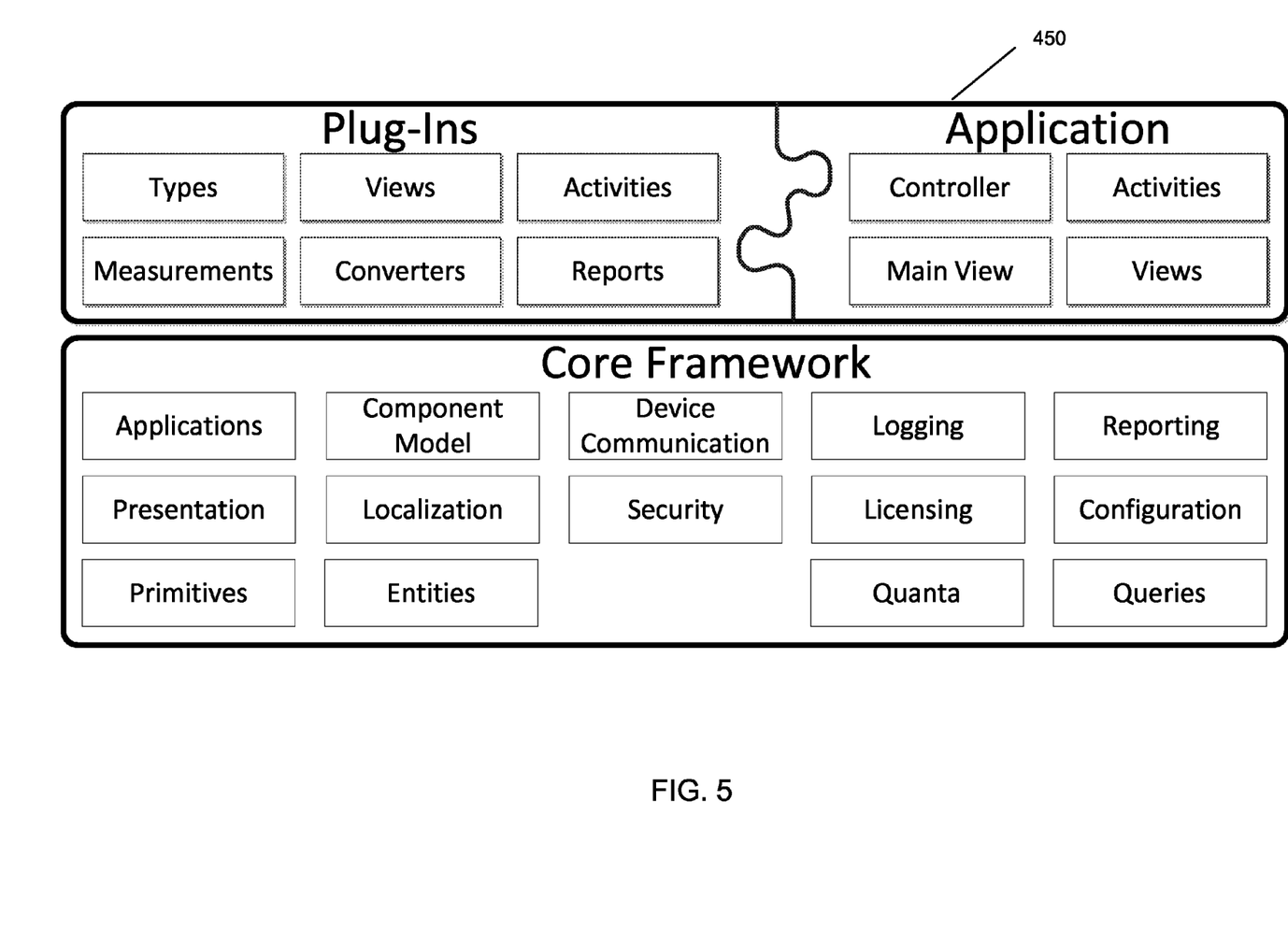
FIG. 5 shows logical components of an example vital monitoring workstation of the system of FIG. 4.

Referring now to FIG. 5, additional details of the VM workstation 450 are shown.

In this embodiment, various applications and services built on the platform 420 (e.g., VM workstation 450, ECS 470 and EGS 430) are a compilation of the components shown in FIG. 5. In this example, the architecture the VM workstation 450 is shown.

In this example, the VM workstation 450 includes a plurality of logical components, including applications, plug-ins, and a core framework. These components form a layered architecture in which applications and plug-ins form the upper layer and are dependent upon the definitions and functions implemented in the core framework.

The core framework provides the basic types and interfaces used by applications and plug-ins. The types cover a variety of areas of functionality. The core framework is organized into groups and can be defined by one or more namespaces.

The primitives group represents the basic data structures such as name, gender, address, etc., used by the more complex types and services defined within the core framework.

The entities group defines the basic objects like user, clinician, patient, test, measurement, etc., and operations that can be applied to these objects. The entities group provides a collection of data structures which are used as object-oriented abstractions of entities that are stored in the database. Each entity type typically has an underlying table in the database and each instance of the entity corresponds to a row in that table.

To retrieve entity data stored in the database, the queries group provides capabilities to query the database. In most cases, the application will pass entity data through method arguments, but the query namespace provides a direct way to query the database from within the plug-in. It supports construction of queries using an object-oriented syntax. This group abstracts the user from requiring knowing details on how the objects are stored in the database.

Diagnostic measurements have numerical attributes. To represent these, the quanta types are provided for commonly used quantities such as weight, volume, temperature, pressure etc. These types encapsulate the quantity and include support for commonly used conversion calculations from one unit of measure to another.

The presentation types define common user interface elements such as styles, templates, user controls and dialogs. The platform supports internationalization and localization. The localization types provide support for dynamic culture switching and localization of UI screens.

The security types support authentication and authorization within the system.

The licensing types support software licensing of the system features. They include the ability to check if a specified feature is properly licensed, and the ability to activate a license.

The configuration group provides types that support reading application settings and allow extending this set with custom settings.

The reporting group provides the types needed for formatting, previewing and printing reports using a flexible layout mechanism.

The logging types supports logging application events and custom messages from components and plug-ins.

The device communication group provides an abstraction layer that the application can use to communicate with connected medical devices.

The component model group defines the interfaces that form the base of all extension points defined in the core framework. It also provides types that determine how plug-ins and components can declaratively specify their capabilities (exports) and dependencies (imports) through metadata.

The types in the core framework's applications namespace extend the base component model types to define interfaces that form the contracts between plug-ins and applications. These interfaces are defined in terms of activities. The Application namespace provides a predefined library of activity interfaces, one for each extension point.

In this example, an activity is the most basic unit of work. Each application is divided into a series of tasks or workflows. Each workflow can be further imagined as a series of steps or activities.

Applications such as the VM workstation 450 include workflows that execute one or more activities that are supplied by plug-ins. Executing an application workflow implies executing the constituent activities. The library of activity interfaces for plug-ins to implement provided by the core framework allows plug-ins to control what exactly they need to do when application workflows invoke them.

The core framework's component model group defines the base activity interface. The Application group extends this to define a number of pre-defined activity interfaces targeting supported workflows such as capturing a test, reviewing a test etc. Plug-ins can choose to participate in the application's workflow by implementing the interface of the activity involved in that workflow.

Each application includes basic infrastructure needed to coordinate and execute application workflows. This infrastructure includes an application controller which is responsible for providing an execution environment for activities. This includes setting up the main view, which is the root window of the application and initializing other services needed by the application.

The application controller represents the logic that defines the workflows. Workflows can be either sequential or state driven in nature. State driven workflows respond to user's interaction with the application. An example of a sequential workflow is application startup, which follows a predefined sequence. An example of a workflow that is state driven is the test compare workflow that requires input from the user to complete.

Activities often pass visual elements to the application. The application workflow then determines how to appropriately display these visual elements within the screens of the application.

Plug-ins are used to customize the application behavior. Plug-ins can extend various applications and services, as described herein.

Plug-ins are typically written to define new or modify existing medical diagnostic measurements via the Entities namespace. The core framework provides the infrastructure to add these measurement types to the platform 420. Plug-ins can also define converters for transforming data into types that can be consumed by the platform 420.

Plug-ins can provide activity implementations to add custom behavior to an application. These activities may provide views to support user interaction. Plug-ins may also define custom layout for reports.

The VM workstation 450 is a client application designed to aid the clinical user in workflows such as acquiring, analyzing and processing diagnostic data and recording other pertinent observations during a medical diagnostic test. The extensibility of the VM workstation 450 comes from the ability of developers to create plug-ins that will be utilized by the application in each of these supported workflows.

For the platform 420, a plug-in is a collection of components that can be "plugged in" to add functionality to applications or services built on the platform. The amount of functionality defined in a plug-in is configurable. Components can be gathered into one plug-in, or separated out amongst several, as needed or desired.

Each application has a designated location for plug-ins. Once the code needed for a plug-in has been developed, it is compiled into .NET assemblies. These assemblies are deployed to a subdirectory of the plug-ins location along with a manifest file.

When the VM workstation 450 starts, it recursively searches the plug-ins installation location and creates a list of assemblies to load by analyzing the manifest files. In this example, the application uses the Managed Extensibility Framework (MEF) library in .NET to load the assemblies into a catalog for inclusion in the VM workstation 450. The application finds the plug-in types in the catalog and includes them in the appropriate workflows and UI touch points.

In some examples, an approval process (e.g., by an administrator and/or manufacturer of the platform 420) is required before a plug-in can be registered and executed by the VM workstation 450. In other examples, no approval is needed.

The plug-ins are used to extend the functionality of the VM workstation 450. For example, one of the fundamental ways in which the VM workstation can be extended is through defining new test and measurement types. In the platform 420, a test represents a diagnostic procedure performed on a patient. Diagnostic tests may entail recording many medical measurements. A test can be thought of as a container that holds these measurements.

To support new diagnostic procedures, new test and measurement types can be defined and registered with the platform 420. Measurement definitions are registered independently of the test definitions and thus can be reused across various Test types.

Plug-ins can be created that provide a user with an interface to manually enter and save the results of a test. Alternately, the plug-in may provide the user interface necessary to acquire the test using a medical device directly connected to the VM workstation 450.

The VM workstation 450 provides the ability to review and update test instances that have been saved. Plug-ins can be created to add new views for the review of test and measurement data. Plug-ins can also provide the capability to update new or previously existing test instances.

To help end users examine a patient's medical history, the VM workstation 450 can be extended via plug-ins to allow users to compare multiple test instances of the same test type in a single view.

Plug-ins can be created to display a simplified summary of the test data. This allows the application to show a snapshot of the patient's most recent test data. The VM workstation 450 provides the ability to generate a variety of reports on test data. New report templates can be created via plug-ins to custom format the report data. Further, the VM workstation 450 provides the ability to define custom settings and manage them on an individual or group basis.

Medical devices (e.g., medical device 480) directly communicate with the VM workstation 450 through the Device Connectivity Layer (DCL). Plug-ins can be written for the DCL to extend the list of supported devices, message formats, and communication protocols. Plug-ins can be written to support native and third party devices, such as new medical devices manufactured by the manufacturer of the platform 420 or third parties, that make use of the Welch Allyn Communication Protocol (WACP), as well as devices that make use of other proprietary protocols.

Figure 6:
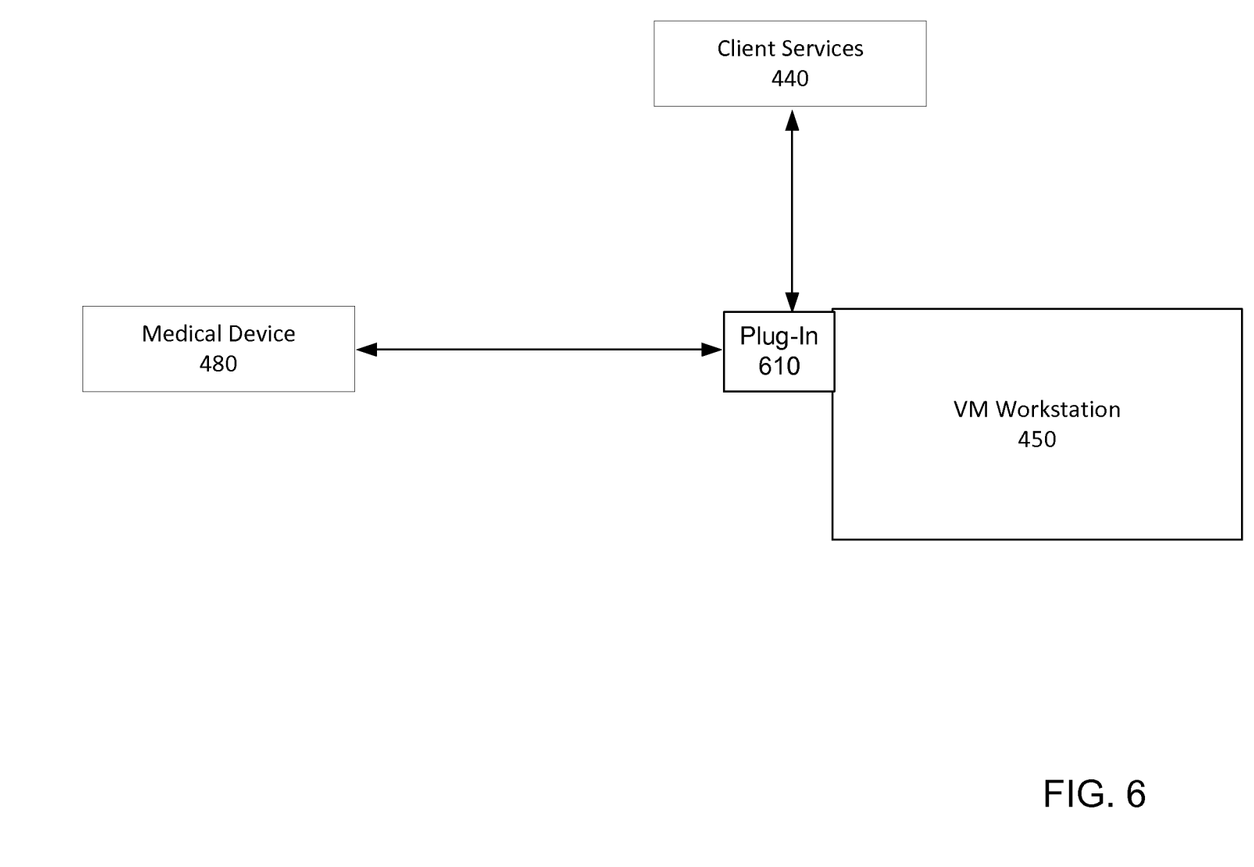
FIG. 6 shows a schematic representation of the vital monitoring workstation of FIG. 5.

Referring now to FIG. 6, a schematic representation of the VM workstation 450, the client services 440, and the medical device 480 is shown. In this example, the VM workstation 450 executes a plug-in 610 that extends the functionality of the VM workstation 450.

For example, the plug-in 610 can extend the functionality of the VM workstation 450 so that the VM workstation 450 can communicate with the medical device 480 if the medical device is a new device manufactured after the manufacture and deployment of the VM workstation 450.

For example, assume that the medical device 480 is a device that measures pulse oximetry (other examples include resting electrocardiogram (ECG), stress ECG, and spirometry). Assume that the platform 420, including the VM workstation 450, was not manufactured to communicate with such a device. The plug-in 610 is created and registered with the VM workstation 450. Upon execution, the plug-in 610 extends the capabilities of the VM workstation 450 so that the VM workstation 450 can communicate with the medical device 480. For example, the VM workstation 450 can instruct the medical device 480 to take a pulse oximetry reading and report the result to the VM workstation 450.

In addition, the plug-in 610 (or in some examples, a separate plug-in can be used) can be programmed to allow the workstation 450 to communicate the pulse oximetry reading to the client services 440. In this manner, the functionality of the VM workstation 450 is extended so that the VM workstation 450 can communicate with the new medical device 480, command the new device 480 to take and report readings, and communicate those readings to the client services.

In yet other embodiments, the plug-in 610 can also allow the VM workstation 450 to manipulate the readings from the medical device 480. For example, the plug-in 610 can allow the VM workstation 450 to trend multiple pulse oximetry readings and present the results in a graphical format to the user of the VM workstation 450. Other functionality is possible.

Although only a single plug-in 610 is illustrated, a plurality of plug-ins can be used to further extend the functionality of the VM workstation 450. Further, similar plug-ins can be used to extend the functionality of other components of the platform 420, such as the ECS 470 and EGS 430.

There are significant advantages to the use of plug-ins as described herein. For example, the plug-ins can be used to extend the functionality of devices, such as the VM workstation 450, to allow the devices to communicate with and manipulate data from new devices, as well as new test types. This is accomplished without requiring the devices to be upgraded or reprogrammed. Instead, the relevant plug-ins can simply be registered and executed by the devices to extend the functionality.

Figure 7:
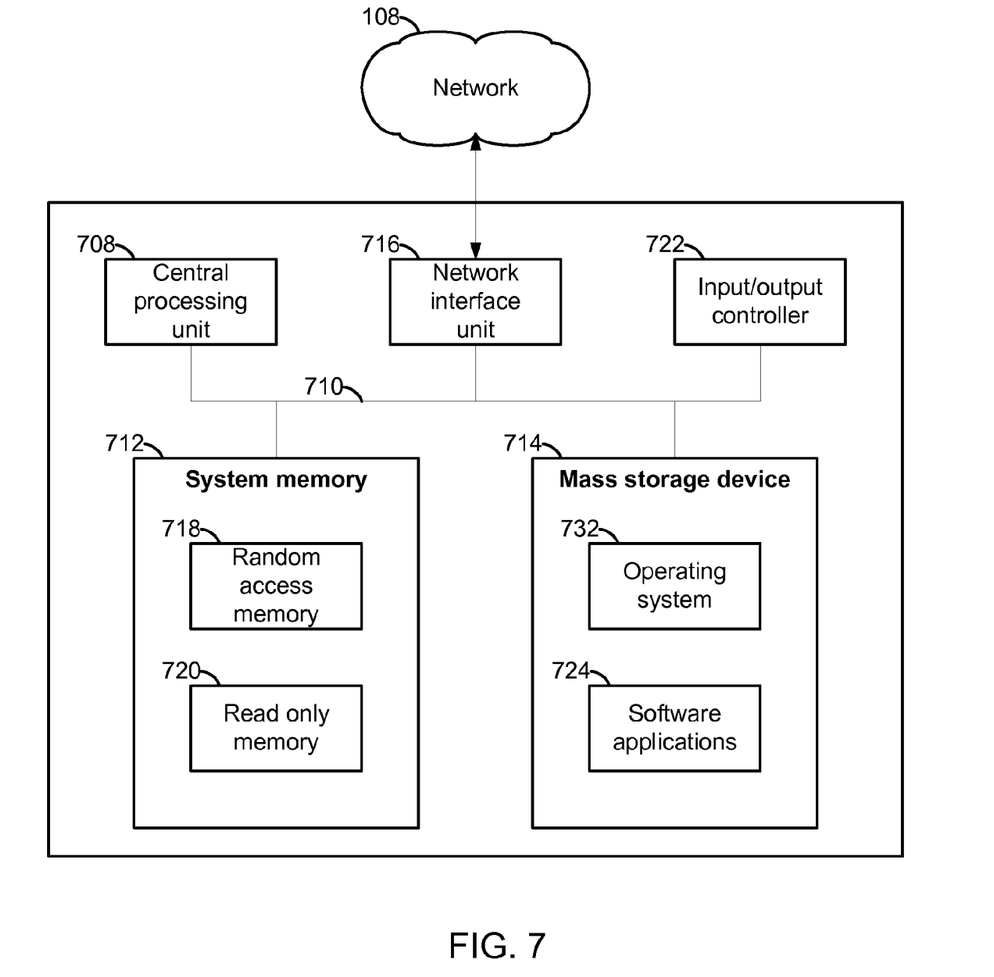
FIG. 7 shows various components of an example vital monitoring workstation of the system of FIG. 4.

FIG. 7 illustrates example physical components of a computing device. In this embodiment, various applications and services built on the platform 420 (e.g., VM workstation 450, ECS 470 and EGS 430) are a compilation of the components shown in FIG. 7. In this example, the architecture of the VM workstation 450 is shown.

As illustrated in the example of FIG. 7, the VM workstation 450 includes at least one central processing unit ("CPU") 708, a system memory 712, and a system bus 710 that couples the system memory 712 to the CPU 708. The system memory 712 includes a random access memory ("RAM") 718 and a read-only memory ("ROM") 720. A basic input/output system containing the basic routines that help to transfer information between elements within the VM workstation 450, such as during startup, is stored in the ROM 720. The VM workstation 450 further includes a mass storage device 714. The mass storage device 714 is able to store software instructions and data.

The mass storage device 714 is connected to the CPU 708 through a mass storage controller (not shown) connected to the bus 710. The mass storage device 714 and its associated computer-readable data storage media provide non-volatile, non-transitory storage for the VM workstation 450. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the VM workstation 450 can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the VM workstation 450.

According to various embodiments of the invention, the VM workstation 450 may operate in a networked environment using logical connections to remote network devices through the network 108, such as a local network, the Internet, or another type of network. The VM workstation 450 connects to the network 108 through a network interface unit 716 connected to the bus 710. It should be appreciated that the network interface unit 716 may also be utilized to connect to other types of networks and remote computing systems. The VM workstation 450 also includes an input/output controller 722 for receiving and processing input from a number of other devices, including a keyboard, a mouse, a touch user interface display screen, or another type of input device. Similarly, the input/output controller 722 may provide output to a touch user interface display screen, a printer, or other type of output device.

As mentioned above, the mass storage device 714 and the RAM 718 of the VM workstation 450 can store software instructions and data. The software instructions include an operating system 732 suitable for controlling the operation of the VM workstation 450. The mass storage device 714 and/or the RAM 718 also store software instructions, that when executed by the CPU 708, cause the VM workstation 450 to provide the functionality of the VM workstation 450 discussed in this document. For example, the mass storage device 714 and/or the RAM 718 can store software instructions that, when executed by the CPU 708, cause the VM workstation 450 to register the plug-in 610 and other operations.

Although components of the VM workstation 450 are depicted in FIG. 7, other devices, such as the medical devices 200, 480, 490, can include similar components.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A system for healthcare diagnostic applications comprising:
   a computing device including memory and a processor that, when executing instructions stored on the memory, creates:
   a client-side framework defining elements for use by platform client applications;
   a composite application framework supporting extensible modules, the composite application framework supporting construction of composite applications in which functionality is implemented by a container application which hosts plug-in modules to support specific diagnostic functions;
   a plug-in module extending platform applications;
   a composite application combining base application code with plug-in modules to support a set of clinical functions;
   a domain-specific framework for defined clinical measurement domains, wherein the domain-specific framework shares certain common code and resources with other modules and contain domain-specific expandable sets of sensor measurement plug-ins which obtain physiologic data of a type covered by a domain; and
   the plug-in module provides an interface implementation with methods to serialize and de-serialize the measurement-derived class, and a schema which describes the measurement's serialized form which can be used by a server to efficiently store and search within measurement data.

2. The system of claim 1, further comprising:
   a remote authentication service providing a means to manage access to wireless networks, internal networks, and the Internet;
   a device connection protocol service providing a simple directory of TCP/IP-based services, allowing devices which use TCP/IP communication a means in which to lookup an address and a port of the service with which they wish to communicate;
   a device connectivity service acting as a relay/translator for both wired and wireless devices, allowing direct communication to and from supported devices to the software platform, the device connectivity service providing an interoperability layer between device-level communication protocol-based messaging and platform services;
   a login service providing methods to confirm and track application authorization;
   a data service providing Create-Retrieve-Update-Delete operations for basic data entities of a platform repository;
   an admin service providing access to administration functions of the platform services;

an event service providing a general publish-and-subscribe mechanism to communicate via event messages within a system; and a service provider running on the server performing tasks in support of the platform services, the services interfacing with external systems such as an HIS or file system.

3. The system of claim 1, wherein the plug-in module provides two or more views, the views being user interface elements for the acquisition and review of test measurement-specific data, these views being registered with the composite application so that an application may invoke an appropriate view when a request to acquire or review the corresponding test type is made.

4. The system of claim 1, wherein the plug-in module implements report elements, the report elements being visualizations of test measurement-specific data which is incorporated into a report, the report elements being registered with the composite application which makes them available for creating and processing of report templates.

5. The system of claim 1, wherein the plug-in module defines several report templates, the report templates incorporating the report elements the plug-in module defines and support both the print function of various views defined by the plug-in module and standard reports for the plug-in's test measurement type.

6. The system of claim 1, wherein the client-side framework includes:

a service manager functioning as a class factory for the service proxy classes of the platform services, the service manager being used by client-side code which directly communicates with the services;

an entity module creating an object-oriented abstraction for the platform functionality, the entity module abstracting the service functions as entity objects and methods, the objects including patient, visit, test, user, clinician, group, configuration and audit entry;

an entity manager acting as a class-factory and manager of the entity objects;

a general logging mechanism being used by applications to maintain a log of application events;

a general reporting mechanism which can be used by applications to generate reports using templates and entity data;

wherein the client-side framework defines data types being shared by application and framework modules, the data types including basic quantity types and queries;

wherein the client-side framework defines user interface elements including styles, templates, user controls and dialogs, the user interface elements supporting a common look-and-feel for platform-based applications; and wherein the client-side framework supports methods to communicate with devices.

7. The system of claim 1, wherein the composite application includes:

an inversion-of-control container allowing loose coupling of application components by allowing the components to register interfaces they export and resolve interfaces they need from a registered list of interfaces; and a module framework defining attributes and classes which support the construction of modules which can be loaded and managed by the composite application.

8. The system of claim 1, wherein the domain-specific framework defines types of data of measurement classes and other domain-specific types shared by modules and plug-ins for the domain, and defines user interface elements common to modules and plug-ins in the domain.

9. The system of claim 1, wherein the composite application includes:

a screen management module controlling how user interface elements are laid out on the screen;

a navigation module controlling how a user moves from screen to screen within an application;

a patient management module allowing patient information to be created, retrieved, and modified;

a test management module allowing test acquisition to be initiated, test results to be saved, retrieved and reviewed; and a configuration module allowing settings for the application and its plug-ins to be defined and stored.

10. The system of claim 1, wherein the plug-in module is a vitals plug-in which facilitates vitals measurement acquisition, review, editing, batch import, and configuration.

11. The system of claim 10, wherein the vitals plug-in is an extensible module that uses plug-in modules for extended set of measurements, each plug-in following a defined pattern so that new plug-ins conforming to the pattern can be created and added for future measurements.

12. The system of claim 10, wherein the vitals plug-in communicates to devices through USB or serial port using a framework device connectivity layer library.

13. The system of claim 10, wherein the vitals plug-in sends requests to devices and wait for responses to decipher and process, each measurement being responsible for its own data processing.

14. The system of claim 10, wherein the vitals plug-in allows entering data manually when device data is not available and allows manual overwriting of device data when needed.

15. The system of claim 10, wherein the vitals plug-in provides assets to review test/measurement information, the data being organized in historical order with limited set of information or with extended set of information, each test being reviewed with a full set of information.

16. The system of claim 10, wherein the vitals plug-in allows editing of measurement information after test is taken, is installed as a part of the platform installation, provides assets to change its own configuration, and provides default settings to the assets.

17. The system of claim 1, wherein the software platform includes an application being an extensible composite client platform for hosting functional modules that interact with the platform services, the application providing application services, along with access to the platform services via client-side framework elements.

* * * * *